United States Patent [19]

Arnaout

[11] Patent Number: 5,424,399
[45] Date of Patent: Jun. 13, 1995

[54] HUMAN CR3α/β HETERODIMERS

[75] Inventor: M. Amin Arnaout, Chestnut Hill, Mass.

[73] Assignee: The Children's Medical Center Corporation, Boston, Mass.

[21] Appl. No.: 78,871

[22] Filed: Jun. 16, 1993

Related U.S. Application Data

[63] Continuation of Ser. No. 539,842, Jun. 18, 1990, abandoned, which is a continuation-in-part of Ser. No. 212,573, Jun. 28, 1988, abandoned.

[51] Int. Cl.$^6$ .............................................. C07K 14/705
[52] U.S. Cl. .................................. 530/350; 435/69.1; 536/23.5
[58] Field of Search ............... 530/324, 350; 435/69.1, 435/69.4; 514/2

[56] References Cited

U.S. PATENT DOCUMENTS 4,840,793  6/1989  Todd, III et al. ................. 424/85.8

OTHER PUBLICATIONS

Traunecker et al Immunology Today vol. 10, 29–32, 1989.
Dana et al. Proc. Nat'l Acad Sci. USA, vol. 88, pp. 3106–3110, Apr. 1991.
Kishimoto et al "Cloning of the β-Subunit of the Leukocyte Adhesion Proteins" Cell vol. 48 pp. 689–690, Feb. 28, 1987.
Corbi et al. "The Human Leukocyte Adhesion Protein Mac-1 (Complement Receptor Type 3) α Subunit", J. Biol. Chem. vol. 263(25) 12403–12411, Sep. 5, 1988.
Smith et al "Blocking of HIV-1 Infectivity by a Soluble, Secreted Form of the CD4 Antigen" Science vol. 238, pp. 1704–1707, Dec. 1987.
Arnauot et al., J. Clin. Invest. 72:171–179, 1983.
Dana et al., J. Immunol. 137:3259–3263, 1986.
Wallis et al., J. Immuno. 135:2323–2330, 1985.
Arnaout et al., New Eng. J. Med. 312:457–462, 1985.
Dana et al., J. Clin. Invest. 73:153–159, 1984.
Beatty et al., J. Immunol 131:2913–2919, 1983.
Law et al., Eur. Mol. Biol. Organ. J. 6:915–919, 1987.
Todd et al., Hybridoma 1:329–337, 1982.
Pierce et al, Biochem. Biophys. Acta. 874:368–371, 1986.
Miller et al., J. Immunol. 138:2381–2383, 1987.
Cosgrove, Proc. Nat'l. Acad. Sci. USA 83:752–756, 1986.
Sastre et al., Proc. Nat'l Acad. Sci. USA 83:5644–5468, 1986.
Arnaout et al., J. Clin. Invest. 74:1291–1300, 1984.
Todd et al., J. Clin. Invest 74:1280–1291, 1984.
Simpson et al., J. Clin. Invest. 81:624, 1988.
Arnaout et al., J. Clin. Invest. 85:977, 1990.
Ruoslahti et al., Science 238:491, 1987.
Hynes et al., Cell 48:549, 1987.
Arnaout et al., Blood 75:1037, 1990.
Arnaout et al., J. Cell Biol. 106:2153, 1988.
Hickstein et al., Proc. Natl. Acad. Sci USA 86:257–261, 1989.
Larson et al., J. Cell. Biol. 108:703, 1989.
Corbi et al., EMBO, J. 6:4023, 1987.
Pytela et al., EMBO J. 7:1371, 1988.
Vedder et al., J. Clin. Invest. 81:939, 1988.
Hutchings et al., Nature 348:639, 1990.
Carlos et al., Immunol. Rev. 114:5, 1990.
Dana et al., The Journal of Immunology, vol. 137, pp. 3259–3263, No. 10, Nov. 15, 1986.

(List continued on next page.)

Primary Examiner—Garnette D. Draper
Assistant Examiner—John D. Ulm
Attorney, Agent, or Firm—Fish & Richardson

[57] ABSTRACT

The invention features human CR3α recombinant or synthetic peptide capable of inhibiting a CR3-mediated immune response, a purified DNA encoding a human CR3α peptide, and a method of controlling any phagocyte-mediated tissue damage such as that associated with reduced perfusion of heart tissue during acute cardiac insufficiency. As used herein, a human CR3α recombinant peptide is a chain of amino acids derived from recombinant CR3α-encoding cDNA, or the corresponding synthetic DNA.

2 Claims, 4 Drawing Sheets

OTHER PUBLICATIONS

Arnaout et al., Relative Contribution of the Leukocyte Molecules Mo1, LFA-1, and p150,95 (LeuM5) in Adhesion of Granulocytes . . . Endothelium is Tissue- and Stimulus-Specific, J. Cellular Physiology 137:305–309, 1988.

Arnaout et al., Deficiency of a Granulocyte-Membrane Glycoprotein (gp150) in a Boy with Recurrent Bacterial Infections, The New England Journal of Medicine 306:693–699, 1982.

Arnaout et al., Molecular Cloning of the α Subunit of Human and Guinea Pig Leukocyte Adhesion Glycoprotein Mo1: Chromosomal Localization and . . . α Subunits of Integrins, Proc. Natl. Acad. Sci. USA 85:2776–2780, 1988.

Beller et al., Anti-Mac-1 Selectively Inhibits the Mouse and Human Type Three Complement Receptor, J. Exp. Med. 156:1000–1009, 1982.

Mentzer et al., Adhesion of T Lymphocytes to Human Endothelial Cells is Regulated by the LFA-1 Membrane Molecule, J. Cellular Physiology 126:285–290, 1986.

```
L  T  Q  T  C  E  T  L  K  L  Q  L  P  N  C  I  E  D  P  V  S  P  I                                          713
gtgctgcgctgactcttctctgtgggaacgccattgtctgtctcggaacctgtccggccagtgctg                                            736
V  L  R  L  N  F  S  L  V  G  T  P  L  S  A  F  G  N  L  R  P  V  L
gcggagggatgctcagagactccagacctcttgttcccttgagaagatgtgcaatgacaacatc                                              759
A  E  D  A  Q  R  L  F  T  A  L  P  P  E  K  N  C  G  N  D  N  I
tgccaggatgaccttcagcatcacctttcagttcatgagcctgacctgtggtgggtgggcccggg                                             782
C  Q  D  D  L  S  I  T  F  S  F  M  S  L  D  C  L  V  V  G  G  P  R
gagtctagcgtgacagtgactgtgagaatgatggtgaggactcctacagagacacaggtcacccttcttc                                        805
E  F  N  V  T  V  T  V  R  N  D  G  E  D  S  Y  R  T  Q  V  T  F  F
ttcccgcttgacctgtcctacgggaagtgtcctccaactctccagaaccagcgatcctggcgc                                               828
P  P  L  D  L  S  Y  R  K  V  S  T  L  Q  N  Q  R  S  Q  R  S  W  R
ctgacctgtgactctcccaccgaagtctctgggcttgccctgaagagcacagtgcagcataaac                                              851
L  A  C  E  S  A  S  T  E  V  S  G  A  L  K  S  T  S  C  S  I  N
cacccatctctcccggaaaactcagaggtcaccttagtatcacgttgatgtagctctaaggcttcc                                            874
H  P  I  F  P  E  N  S  E  V  T  P  N  I  T  F  D  V  D  S  K  A  S
cttggaaacaactgctcctcaaggccaatgtgaccagtgagacaacatgccagaaccacaaacc                                              897
L  G  N  K  L  L  K  A  N  V  T  S  E  N  N  H  P  R  T  N  K  T
gaattccaactgtgaactccacgagctgcctgaaatatgctgtcacatgtgtcctacactggggtctccact                                      920
E  P  Q  L  E  L  P  V  K  Y  A  V  Y  M  V  V  T  S  H  G  V  S  T
aaatatctcaacttcacggcctcagagagatcaataccagtgtcatgcagcaatatcagttcagcaac                                          943
K  Y  L  N  F  T  A  S  E  N  T  S  R  V  M  Q  Y  Q  V  S  N
ctgggcagagaggagccccatcagctcagcctggtttcttgtgccccgtccggctgaaccagactgtcata
```

FIG. 1c

```
L  G  Q  R  S  P  P  I  S  L  V  F  L  V  P  V  R  L  N* Q  T  V  I
tgggaccgccccagtcacctctcgagaacctctcgagtacgtgccaccaagagcttgccc      966
W  D  R  P  Q  V  T  P  S  E  N* L  S  S  T  Ⓒ  H  T  K  E  R  L  P
tctcactccgactttctgagcttcgaaggccccgtgaacgtgctccatcgtctgcag        989
S  H  S  D  F  L  A  E  L  R  K  A  P  V  V  N* Ⓢ  I  A  V  Ⓒ  Q
agaatccgagtgtgacatcccgtttcttggcatccaagaattcaatgctacccctcaaaggcacctc  1012
R  I  Q  Ⓒ  D  I  P  F  F  G  I  Q  E  F  N* A  T  L  K  G  N* L
tcgtttgactgtacatgaaccttccacctcctgatcgtgacagtcgtgagatctttgttt       1035
S  P  D  W  Y  I  K  T  S  H  N  L  L  I  V  S  T  A  E  I  L  F
aacgattccgttcaccgtgcaggggtcgtgtgtgaggcgagacctcgtgagtcctgagacaaagtg  1058
N  D  S  V  F  T  L  P  G  Q  G  A  F  V  R  Q  T  E  T  K  V
gagccgttcgagcgtcccaaccctgctcatcgtgcagtctctgtcgggactgctgctcctg     1081
E  P  F  E  V  P  N  P  L  P  L  I  V  S  S  V  G  L  L  L  L
gccctcatcaccgccgtgtacaagctgcttcttcaaggcatacaaggcatgatgagtgaa      1104
A  L  I  T  A  A  L  T  K  L  G  F  F  K  R  Q  Y  K  D  M  M  S  E
ggggtccccggggccgaacccagtag                                       1127
G  G  P  P  G  A  E  P  Q  .                                    1136
```

FIG. 1d

HUMAN CR3α/β HETERODIMERS

This invention, at least in part, was funded by a grant from the United States Government and the Government has certain rights in the invention.

This is a continuation of application Ser. No. 07/539,842, filed Jun. 18, 1990, now abandoned, which is a continuation in part of application Ser. No. 07/212,573, filed on Jun. 28, 1988, now abandoned.

BACKGROUND OF THE INVENTION

This invention relates to controlling the cellular immune/inflammatory responses, particularly phagocyte-mediated tissue injury and inflammation.

Circulating phagocytic white blood cells are an important component of the cellular acute inflammatory response. It is believed that a number of important biological functions such as chemotaxis, immune adherence (homotypic cell adhesion or aggregation), adhesion to endothelium, phagocytosis, antibody-dependent cellular cytotoxicity, and histaminase and lysosomal enzyme release are mediated by a leukocyte surface glycoprotein receptor, known as complement receptor type 3 (CR3), also known as Mol, CD11b/CD18, Mac-1 or MAM. See, Arnaout et al., *J. Clin. Invest.* 72:171–179 (1983), and references cited therein; Dana et al., *J. Immunol.* 137:3259–3263 (1986); Wallis et al., *J. Immunol.* 135:2323–2330 (1985); Arnaout et al., *New Eng. J. Med.* 312:457–462 (1985); Dana et al., *J. Clin. Invest.* 73:153–159 (1984); and Beatty et al., *J. Immunol.* 131:2913–2919 (1983).

CR3 consists of two noncovalently associated subunits. Kishimoto et al., *Cell* 48:681–690 (1987); Law et al., *Eur. Mol. Biol. Organ. J.* 6:915–919 (1987). The alpha subunit has an apparent molecular mass of 155–165 kD and associates in a divalent cation-independent manner with a beta subunit of 95 kD. Todd et al., *Hybridoma* 1:329–337 (1982). The beta subunit is common to two other leukocyte surface glycoproteins, LFA-1 and p150,95. In addition to sharing the property of binding to the same beta subunit, CR3, LFA-1, and p150,95 leukocyte adhesion molecules require divalent cations to mediate their adhesion functions, and they have homologous $NH_2$-termini. Pierce et al., *Biochem. Biophys. Acta.* 874:368–371 (1986); Miller et al., *J. Immunol.* 138:2381–2383 (1987).

Monoclonal antibodies have been used to identify at least two distinct functional domains of CR3, one mediating adhesion and the other mediating binding to the complement C3 fragment (iC3b). See, Dana et al., *J. Immunol.* 137:3259–3263 (1986).

Cosgrove et al., *Proc. Nat'l. Acad. Sci. USA* 83:752–756 (1986) report a human genomic clone which produces "a molecule(s)" reactive with monoclonal antibodies to CR3α (Mac-1 or OKM1).

Sastre et al., *Proc. Nat'l. Acad. Sci. USA* 83:5644–5648 (1986) report a mouse genomic clone coding for the α subunit of mouse complement receptor type 3.

It is believed that CR3 and p150,95 mediate enhanced adhesiveness of activated phagocytes through increased expression of these proteins on the surface of activated cells. For example, in granulocytes, these proteins are translocated from intracellular storage pools present in secondary and tertiary granules. Arnaout et al., *J. Clin. Invest.* 74:1291–1300 (1984); Arnaout et al., *New Eng. J. Med.* 312:457–462 (1985); Todd et al., *J. Clin. Invest.* 74:1280–1291 (1984).

Inherited deficiency of CR3 impairs leukocyte adhesion-dependent inflammmatory functions and predisposes to life-threatening bacterial infections. Dana et al., (1984), cited above.

Simpson et al., *J. Clin. Invest.* 81:624 (1988) disclose that a monoclonal antibody directed to an adhesion-promoting domain of CR3α reduces the extent of cardiac damage in dogs associated with myocardial infarction, presumably by limiting reperfusion injury.

SUMMARY OF THE INVENTION

The invention features human CR3α recombinant peptide. As used herein, human CR3α recombinant peptide is a chain of amino acids derived by expression of recombinant CR3α-encoding cDNA, or by expression of the corresponding synthetic DNA. For convenience, the term peptide is used to include all polypeptides regardless of length, including short polypeptides as well as proteins.

The invention also features human CR3α synthetic peptides that include at least one functional CR3 domain capable of inhibiting a CR3-mediated immune response. As used herein, "synthetic peptide" means a peptide derived by expression of recombinant DNA or by chemical synthesis. "CR3-mediated immune response" includes those functions mentioned above: chemotaxis, immune adherence (homotypic cell adhesion or aggregation), adhesion to endothelium, phagocytosis, antibody-dependent cellular cytotoxicity, and histaminase and lysosomal enzyme release. Inhibition of these immune functions can be determined by one or more of the following inhibition assays as described in greater detail below: cell-cell aggregation, phagocytosis, adhesion to endothelium, and chemotaxis.

Preferably, the peptide's functional domain has an amino acid sequence between 7 and 500 amino acid residues; most preferably, the domain is an amino acid sequence derived from the natural CR3α amino acid region that is homologous to a binding region of the yon Willebrand factor encompassing amino acids 134 through 340; or a peptide having one of the amino acid sequences: DIAFLIDGS; FRRMKEFVS; FKILVVITDGE; VIRYVIGVGDA; YYEQTRGGQVSVCPLPRGRARWQCDAV (fibronectin-like collagen binding domain; IL-2-receptor-like region); or KSTRDRLR. The peptide may also be derived from one or more of the metal binding domains of the CR3α peptide and preferably may be derived from the domains encompassing amino acids 358–412, 426–483, 487–553, or 554–614; most preferably, the peptide has one of the amino acid sequences: DVDSNGSTD, DVNGDKLTD, DLTMDGLVD, or DSDMNDAYL.

In another aspect, the invention features purified DNA encoding human CR3α or a synthetic CR3α peptide as defined above. The purified DNA may be cDNA encoding all of the CR3α peptide or a restriction enzyme fragment encompassing part of the CR3α-coding region, or synthetic DNA.

The invention can be used to control the cellular immune response mediated by CR3, where that response is not desired. The invention is particularly advantageous in that it avoids introduction of proteins of non-human species, such as non-human antibodies, which (particularly after the first administration) can raise undesired immune responses. It specifically provides a method of controlling damage associated with reduced perfusion of heart tissue (e.g. resulting from myocardial infarction) consisting of administering a therapeutic amount of the above described peptide in a suitable, pharmaceutically acceptable vehicle. It also can be used to treat dialysis leukopenia, a disease state characterized by phagocyte-dependent tissue injury.

In one particular embodiment, the peptide is administered as a heterodimer, with the human CR3β peptide, preferably a truncated (soluble) CR3β peptide that includes the extracellular position of the CR3β peptide and lacks the transmembrane portion. Most preferably, the CR3β portion of the heterodimer is a recombinant protein produced by expressing DNA encoding the truncated CR3β peptide.

Other features and advantages of the invention will be apparent from the following description of the preferred embodiments thereof, and from the claims.

DESCRIPTION OF THE PREFERRED EMBODIMENTS

The drawing will first briefly be described.

Drawing

Figure 1A:
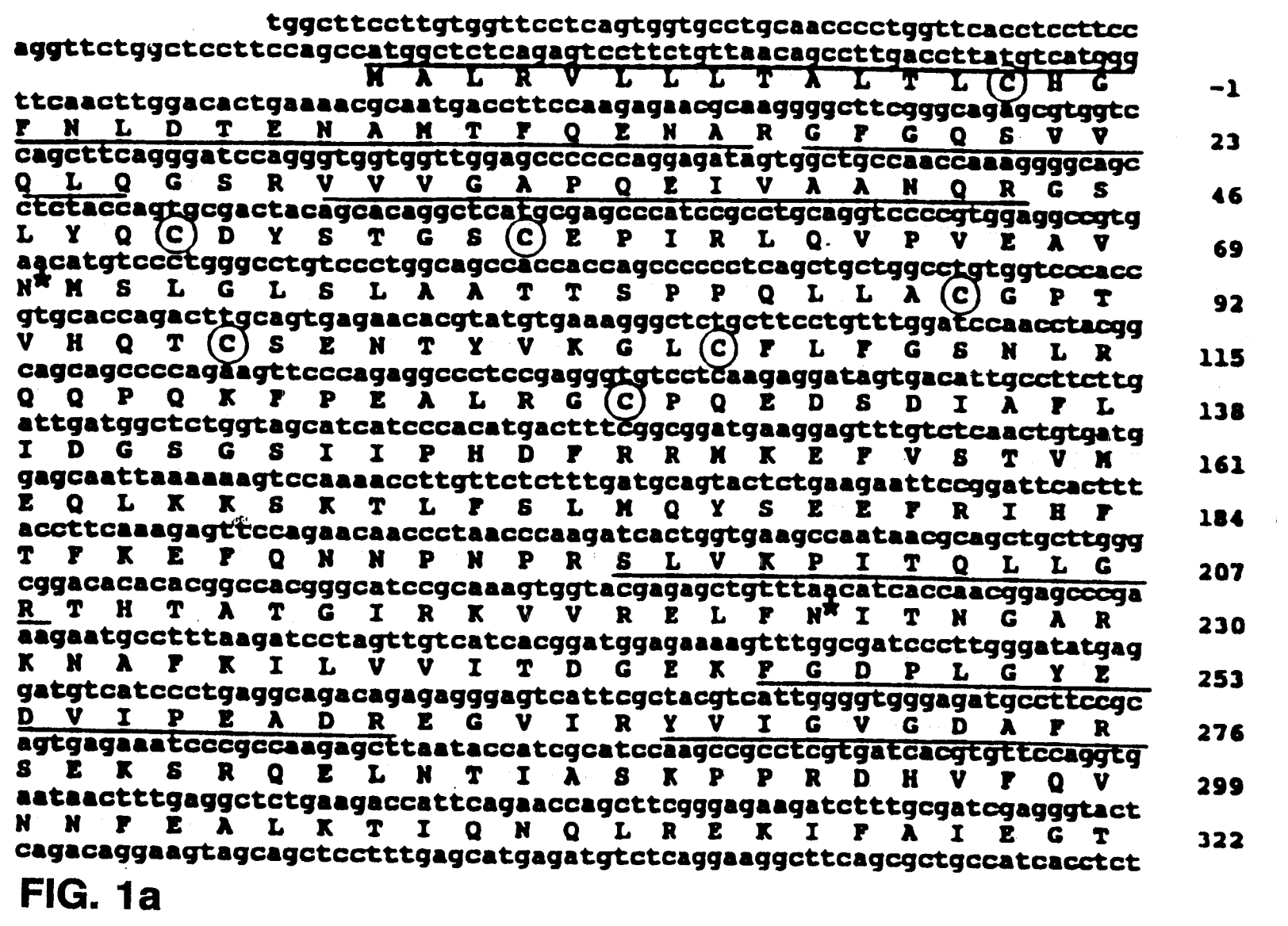
Figure 1B:
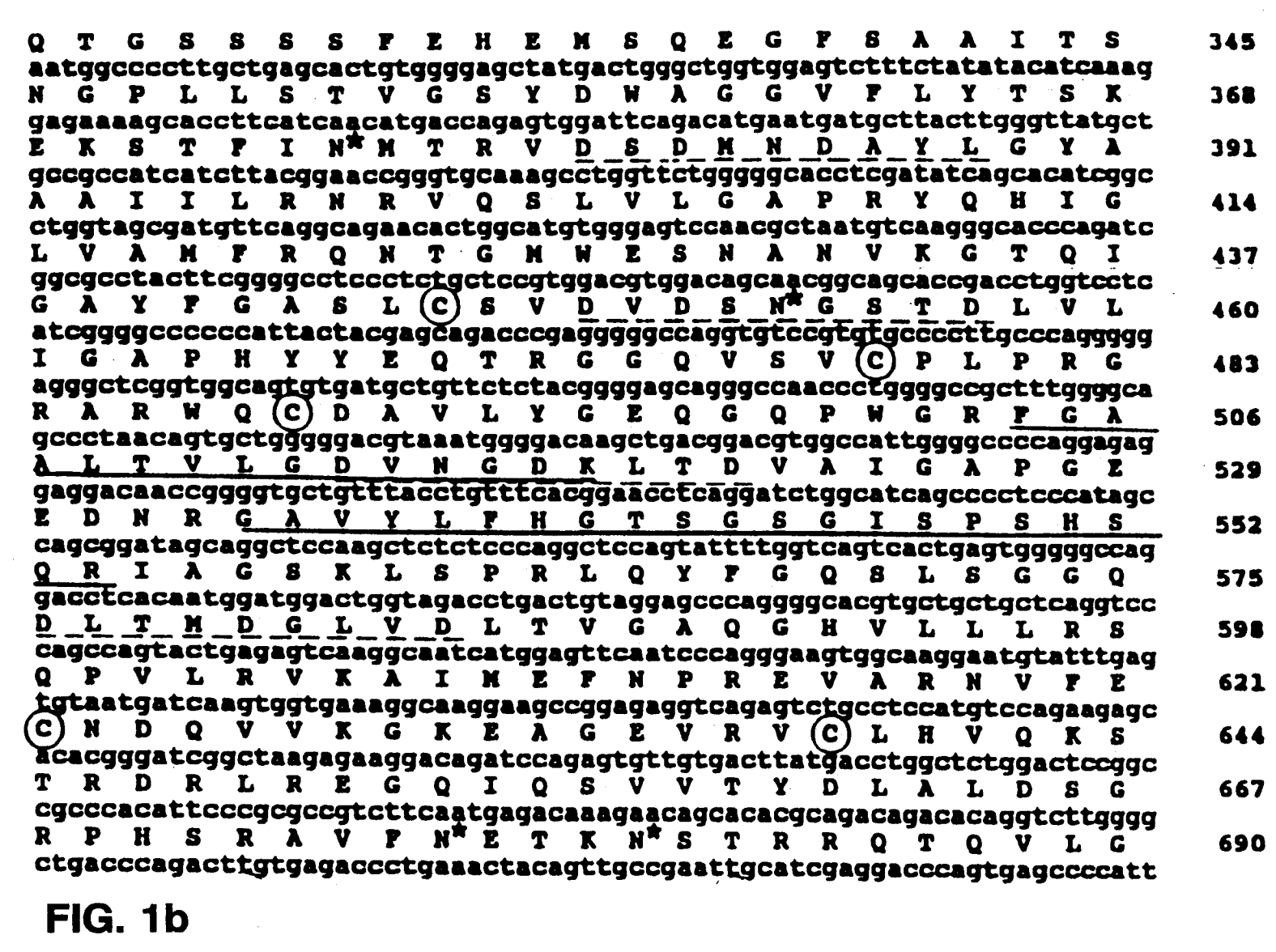

FIG. 1 is the cDNA sequence and deduced amino acid sequence of the open reading frame of human CR3α from Arnout et al., *J. Cell. Biol.* 106:2153-2158 (1988).

CR3α Peptide

The complete human CR3α peptide can be expressed from recombinant DNA encoding the entire α subunit. CR3α peptide fragments according to the invention can be expressed from a cloned restriction enzyme fragment of recombinant DNA or from synthesized DNA. The complete CR3α peptide can be obtained in the following way.

Isolation of a Human CR3α cDNA Clone

A 378 base pair (bp) cDNA clone encoding guinea pig CR3 was used as a probe to isolate three additional cDNA clones from a human monocyte/lymphocyte cDNA library as described in Arnaout et al., *Proc. Nat. Aca. Sci.* 85:2776 (1988); together these three clones contain the 3,048-base nucleotide sequence encoding the CR3α gene shown in FIG. 1.

In order to express CR3α, a mammalian expression vector can be constructed by assembling the above-described three cDNA clones. Appropriate restriction enzyme sites within the CR3α gene can be chosen to assemble the cDNA inserts so that they are in the same translation reading frame. A suitable basic expression vector can be used as a vehicle for the 3,048 bp complete cDNA fragment encoding the human CR3α peptide; the recombinant cDNA can be expressed by transfection into, e.g., COS-1 cells, according to conventional techniques, e.g., the techniques generally described by Aruffo et al., *Proc. Nat'l. Acad. Sci. USA* 84:8573-8577 (1987).

Isolation of CR3α Peptide from Mammalian Cells

The CR3α protein can be purified from the lysate of transfected COS-1 cells, using affinity chromatography and lentil-lectin Sepharose and anti-CR3α monoclonal antibody as described by Pierce et al. (1986) cited above and Arnaout et al., *Meth. Enzymol.* 150:602 (1987). Anti-CR3α monoclonal antibody can be made according to techniques well known in the art using synthetic peptides corresponding to functional domains of the CR3α molecule as the initial immunogen, or it can be purchased from Becton Dickinson, Ortho Pharmaceutical, or other sources.

If the desired CR3α peptide is shorter than the entire protein, DNA encoding the desired peptide can be expressed in the same mammalian expression vector described above using the selected DNA fragment and the appropriate restriction enzyme site, as outlined above. The selected DNA fragment may be isolated according to conventional techniques from one of the CR3α cDNA clones or may be synthesized by standard phosphoamidite methods, as described by Beaucage et al., *Tetrahedron Letters* 22:1859 (1981).

Characterization of the CR3a Polypeptide

The coding sequence of the complete CR3α protein is preceded by a single translation initiation methionine. The translation product of the single open reading frame begins with a 16-amino acid hydrophobic peptide representing a leader sequence, followed by the $NH_2$-terminal phenylalanine residue. The translation product also contained all eight tryptic peptides isolated from the purified antigen, the amino-terminal peptide, and an amino acid hydrophobic domain representing a potential transmembrane region, and a short 19-amino acid carboxy-terminal cytoplasmic domain (FIG. 1). The coding region of the 155-165 kD CR3α (1,136 amino acids) is eight amino acids shorter than the 130-150 kD alpha subunit of p150,95 leukocyte adhesion molecule (1,144 amino acids). The cytoplasmic region of CR3α contains one serine residue that could serve as a potential phosphorylation site. The cytoplasmic region is also relatively rich in acidic residues and in proline (FIG. 1). Since CR3 is involved in the process of phagocytosis and is also targeted to intracellular storage pools, these residues are candidates for mediating these functions. The long extracytoplasmic amino-terminal region contains four metal-binding domains (outlined by broken lines in FIG. 1) that are similar to $Ca^{2+}$-binding sites found in other integrins. Each metal binding site may be composed of two noncontiguous peptide segments and may be found in the four internal tandem repeats formed by amino acid residues 358-412, 426-483, 487-553, and 554-614. The extracytoplasmic region also contains a unique 187-amino acid sequence, beginning at residue 151, which is not present in the homologous alpha subunits of fibronectin, vitronectin, or platelet IIb/IIIa receptors. This sequence is present in the highly homologous alpha subunit of leukocyte p150,95 with 57% of the amino acids identical and 34% representing conserved substitutions. It is known that both Mol and p150,95 have a binding site for complement fragment C3 and this unique region may be involved in C3 binding. This region of CR3α also has significant homology (17.1% identity and 52.9% conserved sustitutions) to the collagen/heparin/platelet GpI binding region of the mature von Willebrande factor (residues 530-713).

The following peptides can be used to inhibit CR3 activity: a) peptide identical to the above-described p150,95-homologous region of CR3α, or a domain thereof, e.g., DIAFLIDGS, FRRMKEFVS, FKILVVITDGE, or VIRYVIGVGDA; b) YYEQTRGGQVSVCPLPRGRARWQCDAV (fibronectin-like collagen binding domain, IL-2-receptor-like region); c) peptides identical to one or more of the four metal binding regions of CR3α, e.g., having one of the following amino acid sequences: DVDSNGSTD, DVNGDKLTD, DLTMDGLVD, DSDMNDAYL;

d) peptides substantially identical to the complete CR3α; or e) other CR3α domains, e.g. KSTRDRLR.

A CR3α peptide, such as one of those described above, can be tested in vitro for inhibition in one of the following five assays: iC3b binding; cell-cell aggregation, phagocytosis, chemotaxis, or adhesion to endothelium; or tested in vivo for controlling damage associated with reduced perfusion of heart tissue, as a result of myocardial infarction.

Inhibition of Granulocyte or Phagocyte Adhesion to iC3b-Coated Erythrocytes or Bacteria The antimicrobial activity of the neutrophil depends to a significant degree on the ability of this cell to establish a firm attachment to its target. For this purpose, neutrophils possess a number of specific cell surface receptors that promote this interaction, such as a receptor which binds to complement C3 (iC3b), e.g. the CR3 receptor. Human neutrophilic polymorphonuclear granulocytes can be isolated from EDTA-anticoagulated blood on Ficoll-Hypaque gradients (Boyum, Scand. J. Clin. Invest. (Suppl.) 21:77 (1968)) modified as described by Dana et al., J. Clin. Invest. 75.:153 (1984)). Phagocytes can be prepared by incubating the mononuclear cell fraction (obtained from Ficoll-Hypaque centrifugation) on plastic petri dishes (Todd et al., J. Immunol. 126:1435 (1981)). Peptides of the invention can be tested for their ability to inhibit iC3b mediated binding of granulocytes to sheep erythrocytes as described in Dana et al., 1984, cited above and Arnaout et al., (1985) cited above.

Inhibition of Phagocytosis

Phagocytosis is an important biological function resulting in clearing of damaged tissue from the body, and in elimination of foreign particles (bacteria, fungi). An in vitro test for inhibition of phagocytosis is described in Arnaout et al., New Eng. J. Med. 306:693 (1982).

Inhibition of Phagocyte Adhesion to Endothelium

Monocytes must cross vascular endothelium during their egress from blood to extravascular tissues. Studies of leukocyte kinetics in animals indicate that acute inflammatory reactions may be marked by a massive increase in transendothelial monocyte/granulocyte traffic. In many chronic inflammatory lesions, perivascular monocytes accumulate in skin windows more slowly than neutrophils, but later become the predominant cell type. In addition monocytes leaving the circulation can rapidly acquire the morphoology of resident tissue macrphages—in some cases within a few hours of their departure from plasma. Thus, vascular endothelium may be considered an important substrate with which monocytes (and granulocytes) must interact during adherence, diapedesis, and differentiation. An in vitro assay for monocyte/granulocyte interaction with the vessel wall consists of binding radiolabeled monocyte/granulocyte preparations to cultured vascular endothelium, as described in Mentzer et al., J. Cell Physiol. 125:285 (1986).

Inhibition Of Chemotaxis

The ability of cells of the immune system to migrate is essential to the cellular immune response that results in tissue inflammation. Therefore, a peptide of the invention can be tested for its ability to inhibit chemotaxis, as described in Dana et al., (1986), cited above.

Cell-Cell Agregation

Granulocyte aggregation will be performed as detailed elsewhere. Arnaout et al., New Engl. J. Med. (1985) cited above. Aggregation will be induced by zymosan-activated autologous serum or with chemotactic peptides, e.g. FMLP. Aggregation will be recorded as incremental change in light transmission [$\Delta T$] using a platelet aggregometer. The reading can be confirmed by phase microscopy.

In Vivo Model for Testing Peptide

Damage to the heart tissue during myocardial infarction can be minimized by administering to an animal an inhibitor of the CR3-mediated immune response. A peptide of the invention may be tested for in vivo effectiveness using animals, e.g., dogs, which have been induced to undergo myocardial infarction. See, e.g. Simpson et al. cited above.

Use

The peptide can be administered intravenously in saline solution generally on the order of mg quantities per 10 kilograms of body weight. The peptide can be administered in combination with other drugs, for example, in combination with, or within six hours to three days after a clot dissolving agent, e.g., Tissue Plasminogen Activator (TPA), Activase, or Streptokinase.

Heterodimer

It may be advantageous to administer the heterodimer formed by the CR3α and CR3β proteins. Expression of the CR3α chain is described elsewhere in this application. Expression of the CR3β chain has been reported by others. See, e.g. Law et al. EMBO J. 6:915-919 (1987); Kishimoto et al. Cell 48:681-690 (1987); Tankum et al. Cell 46:271-282 (1986). The strategies described above or in those reports can be used to obtain CR3β to make such a heterodimer.

Preferably, a secreted form of CR3α/CR3β complex can be produced by co-transfecting COS cells using the cloned CR3α described above and the cloned CR3β. A secreted form of the complex can be produced by known techniques by generating stop codons 5' to the DNA sequences encoding the transmembrane regions of the two subunits. Culture supernatants from COS cells transfected with the combined cDNAs will be used, as described elsewhere, preferably after purification.

Other emobodiments are within the following claims. I claim:

1. A recombinant human CR3 heterodimer comprising
   a) a soluble human CR3α peptide comprising the entire extracellular domain of human CR3α, and being capable of inhibiting a CR3-mediated immune response, said CR3α peptide lacking any of the transmembrane domain of CR3α and said CR3α peptide lacking any of the cytoplasmic domain of CR3α, and
   b) a soluble human CR3β peptide, said human CR3β peptide comprising the extracellular domain of CR3β, and lacking any of the transmembrane domain of CR3β and said CR3β peptide lacking any of the cytoplasmic domain of CR3β,
   said heterodimer being capable of inhibiting a CR3-mediated immune response.

2. A composition comprising the human CR3 heterodimer of claim 1 and a physiologically acceptable carrier.

* * * * *